(12) United States Patent
Bernhardt

(10) Patent No.: US 7,441,954 B2
(45) Date of Patent: Oct. 28, 2008

(54) RADIATION IMAGE CAPTURE APPARATUS

(75) Inventor: Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 347 days.

(21) Appl. No.: 11/352,694

(22) Filed: Feb. 13, 2006

(65) Prior Publication Data

US 2006/0182227 A1  Aug. 17, 2006

(30) Foreign Application Priority Data

Feb. 15, 2005  (DE)  ................ 10 2005 006 894

(51) Int. Cl.
*H01J 35/16*  (2006.01)

(52) U.S. Cl. ..................................... 378/203

(58) Field of Classification Search ............. 378/37, 378/203; 250/506.1, 507.1, 515.1, 516.1, 250/519.1

See application file for complete search history.

(56) References Cited

U.S. PATENT DOCUMENTS

| | | | |
|---|---|---|---|
| 2,205,853 A * | 6/1940 | Jany | 378/171 |
| 3,308,297 A | 3/1967 | Mansker | |
| 4,223,229 A * | 9/1980 | Persico et al. | 250/515.1 |
| 4,581,538 A | 4/1986 | Lenhart | |
| 4,962,515 A * | 10/1990 | Kopans | 378/37 |
| 5,140,710 A * | 8/1992 | Rademacher | 2/432 |
| 5,224,147 A * | 6/1993 | Collin et al. | 378/162 |
| 5,636,259 A * | 6/1997 | Khutoryansky et al. | 378/197 |
| 6,325,538 B1 * | 12/2001 | Heesch | 378/203 |
| 7,331,712 B2 * | 2/2008 | Fischer et al. | 378/203 |
| 2005/0078797 A1 * | 4/2005 | Danielsson et al. | 378/145 |

FOREIGN PATENT DOCUMENTS

| | | |
|---|---|---|
| DE | 19854903 C1 | 10/2000 |
| EP | 0627198 A1 | 12/1994 |
| WO | 03/073939 A1 | 9/2003 |
| WO | 2005/102174 A1 | 11/2005 |

OTHER PUBLICATIONS

05236588 A1, Oct. 27, 2005, Ein-Gal.

* cited by examiner

*Primary Examiner*—Allen C. Ho

(57) ABSTRACT

Radiation image capture apparatus, in particular x-ray apparatus, comprising a radiation source and a radiation receptor, between which an examination object is to be positioned for image capture, a laterally closed apron-like radiation absorption apparatus which can be moved in the direction of the examination object to absorb scattered radiation emitted by the examination object being pro-vided at the radiation source and/or at the radiation receptor.

11 Claims, 2 Drawing Sheets

RADIATION IMAGE CAPTURE APPARATUS

CROSS REFERENCE TO RELATED APPLICATIONS

This application claims priority to the German Application No. 10 2005 006 894.2, filed Feb. 15, 2005 which is incorporated by reference herein in its entirety.

FIELD OF INVENTION

The invention relates to a radiation image capture apparatus, in particular an x-ray apparatus, comprising a radiation source and a radiation receptor, between which an examination object is to be positioned for image capture.

BACKGROUND OF INVENTION

During radiation image capture, for example an x-ray examination, a point radiation source emits the radiation applied to a patient, for example the x-ray radiation. After this radiation has passed through the patient, it strikes the receptor, for example a solid-state radiation detector, an x-ray amplifier or the like. While the radiation is passing though the patient, scatter processes occur, in other words the x -ray radiation which is penetrating or has penetrated the patient is scattered in all directions, so that scattered radiation is radiated by the patient into the environment. This scattered radiation can be a hazard to persons standing in the vicinity of the radiation image capture apparatus, such as the doctor providing treatment or the medical personnel. To suppress this scattered radiation the radiation receptor, thus for example the image amplifier, a film-membrane system, the solid-state radiation detector etc. is often brought as close as possible to the patient. However, this reduces the quality of the image, since a relatively large amount of the x-ray radiation emerging on the patient near the radiation receptor is captured because said radiation receptor is positioned directly on the patient, it being known that this scattered radiation does not contain any image information in contrast to the primary radiation. To counter this, scattered radiation grids are used, which are provided at the capture unit. Another known technique is the "air gap" technique, in which a relatively large distance is left between the patient and the radiation receptor, for example between 20 and 30 cm. A considerable proportion of the scattered radiation emerging on the patient to the radiation receptor side misses the receptor because of the higher solid angle divergence, and thus is not processed by it because of the higher solid angle divergence. The image quality is improved, but the aforementioned radiation hazards for personnel present still occur. However, a radiation hazard results not just from scattered radiation, which essentially emerges on the side of the patient facing the radiation receptor, but also as a result of scattered radiation emerging forward, in other words toward the radiation source, which is likewise harmful for the personnel providing treatment, there generally being a relatively large distance here between radiation source and the examination object.

SUMMARY OF INVENTION

An object of the invention is thus to specify a way of enabling the quantity of scattered radiation emerging into the environment to be reduced.

To achieve this object it is provided according to the invention in the case of radiation image capture of the type mentioned in the introduction that a laterally closed radiation absorption apparatus which can be moved in the direction of the examination object be provided at the radiation source and/or at the radiation receptor to absorb scattered radiation emitted by the examination object.

The inventive apron-like radiation absorption apparatus is particularly advantageously used to close the space between the patient and for example the radiation receptor, thus the air gap mentioned in the introduction, thus virtually forming a radiation tunnel between the patient and the radiation receptor. Any scattered radiation which in this case misses the radiation receptor necessarily strikes the radiation absorption apparatus and is absorbed thereby, and thus can no longer emerge into the environment and hence into personnel standing nearby. In corresponding fashion a radiation absorption apparatus running from the radiation source to the patient can also alternatively or additionally be provided. This also virtually forms a radiation tunnel, the scattered radiation emitted in the forward direction here too being absorbed by the radiation absorption apparatus. The radiation absorption apparatus itself is closed at the sides, producing overall a structure closed on all sides which can collect scattered radiation to a very high degree.

To enable the radiation receptor or the radiation source to be adjusted in respect of the examination object, said adjustment differing in accordance with the examination or type of examination being performed, the radiation absorption apparatus can expediently be moved in the direction of the examination object. This means it is possible to span distances of varying size since the radiation absorption apparatus can be correspondingly moved and thereby positioned. The doctor is thus subject to no restrictions when capturing images as a result of the arrangement of the radiation absorption apparatus.

Thus the inventive radiation image capture apparatus both permits good-quality image capture, since the air gap technique can be used straight away, and achieves maximum protection for nearby personnel against scattered radiation, a high standard of protection being produced if a radiation absorption apparatus is provided only at the radiation receptor, and virtually complete "radiation encapsulization" being achieved if two scattered radiation apparatuses are used in the radiation source and at the radiation receptor.

The radiation absorption apparatus can preferably be moved linearly in respect of the radiation source or the radiation receptor, corresponding linear guides being provided, in or on which the radiation absorption apparatus is guided. It can also easily be relocated in respect of the relevant equipment.

According to a first embodiment of the invention the radiation absorption apparatus can here be rigid and supported at the radiation source and at the radiation receptor in its entirety to enable it to be relocated laterally. The radiation absorption apparatus is for example rectangular or box -shaped, such a shape being provided for example by rectangular solid-state detectors. The shape of the radiation absorption apparatus is geared to the basic shape of the equipment at which it is arranged. In addition, for example, in the case of a round radiation receptor a hollow cylindrical design of the radiation absorption apparatus is also conceivable. In each case it is designed to be rigid, which means it is relocated linearly in its entirety in respect of the relevant device.

Alternatively the radiation absorption apparatus can also consist of sections linked so that they move together and can be relocated in respect of one another, which in the retracted position are arranged essentially in parallel next to one another and in the extended position are arranged one behind the other. The radiation absorption apparatus consists in this embodiment virtually of several mutually linked segments or similar sections. For example, in the case of a rectangular or box-shaped embodiment of the radiation absorption apparatus three such sections are provided on each wall, which can be moved one after the other and taken apart when the radiation absorption apparatus is extended. Alternatively to this embodiment it is also conceivable that the radiation absorption apparatus can be collapsed or folded up, the ability to collapse like an accordion being expedient here both in the case of a rectangular or box-shaped embodiment and of a hollow cylindrical round embodiment.

Alternatively to the laterally closed, single-part shape of the radiation absorption apparatus it is also conceivable to form it from a plurality of separate swivel-mounted sections, which in order to capture an image can be swiveled into a position in which a laterally closed shape is produced. Such an embodiment is provided for example for a radiation absorption apparatus arranged at the radiation source, since from time to time account must be taken here of the radiation array which increases with the increasing distance from the radiation source. In each case the individual swivel sections are designed so that they laterally sufficiently overlap even with a relatively large beam angle, so that a closed shape is produced.

A particularly expedient development provides that the radiation absorption apparatus can be automatically moved using at least a drive motor that can be controlled by means of a control apparatus. If the radiation absorption apparatus is arranged at the radiation receptor for example, in particular a solid-state radiation detector, it can be relocated by the motor in respect of the detector. In this connection either a separate motor can be used, or recourse can be had to a motor frequently provided here which serves to move the detector in respect of the patient.

In this connection it is expedient if at least one sensor is provided to detect the position of the radiation absorption apparatus relative to the examination object, which communicates with the control apparatus, which controls the movement operation as a function of position detection. It is hereby ensured that the movement of the radiation absorption apparatus is terminated at the correct time and that it thus is not extended too far and does not strike the patient. The sensor continuously detects the relative position to the examination object, so that straight away the correct position is detected and the movement operation can be terminated.

If the radiation source and the radiation receptor are arranged on a moveable C-arm, it is expedient if a radiation absorption apparatus when detecting an intended or commenced movement of the C-arm can be moved via the control apparatus away from the examination object in order to avoid a collision therewith and if necessary can again be moved automatically toward the examination object after reaching a new capture position. The radiation source and the radiation receptor can be swiveled freely in known manner via the C-arm relative to the examination object. If an image capture was undertaken in a first position in which the one or both radiation absorption apparatuses were optimally positioned, it must be ensured that when the C-arm is turned on a collision between the radiation absorption apparatus and the patient is avoided. To this end, as soon as it is detected that a movement is to be initiated or has already been initiated, the respective radiation absorption apparatus is moved a short distance away from the patient, so that there is a sufficient swivel or movement clearance. On reaching the new position the respective radiation absorption apparatus is preferably again moved automatically into the optimum position, so that the image capture operation can start immediately.

The radiation absorption apparatus itself can for example have band—or plate-shaped lead, which is accommodated in a sheath, to absorb radiation. This applies for all embodiments described. In the case of a rigid radiation absorption apparatus it is possible to provide only a relatively large-surface band-shaped lead element which extends fully circumferentially over the entire length of the absorption apparatus. In the case of a collapsible apparatus, a plurality of separate band—or plate-shaped lead elements is provided for example, which depending on the embodiment are connected to one another so as to move together or are in another way positioned in respect of one another. Preferably the one or more lead elements are accommodated in a suitable sheath, and preferably have a thickness of approx. 1 mm, this strength of lead being sufficient to absorb the entire scattered radiation that strikes the apparatus.

An alternative possibility is that the lead used for absorption is accommodated in a transparent material, in particular glass, so that the radiation absorption apparatus is totally transparent. Lead glass can thus also be used to construct the absorption apparatus, which gives the doctor the opportunity to observe the region screened by this.

BRIEF DESCRIPTION OF THE DRAWINGS

Other advantages, characteristics and details of the invention emerge from the exemplary embodiments described in the following and on the basis of the drawing. This shows.

DETAILED DESCRIPTION OF INVENTION

Figure 1:
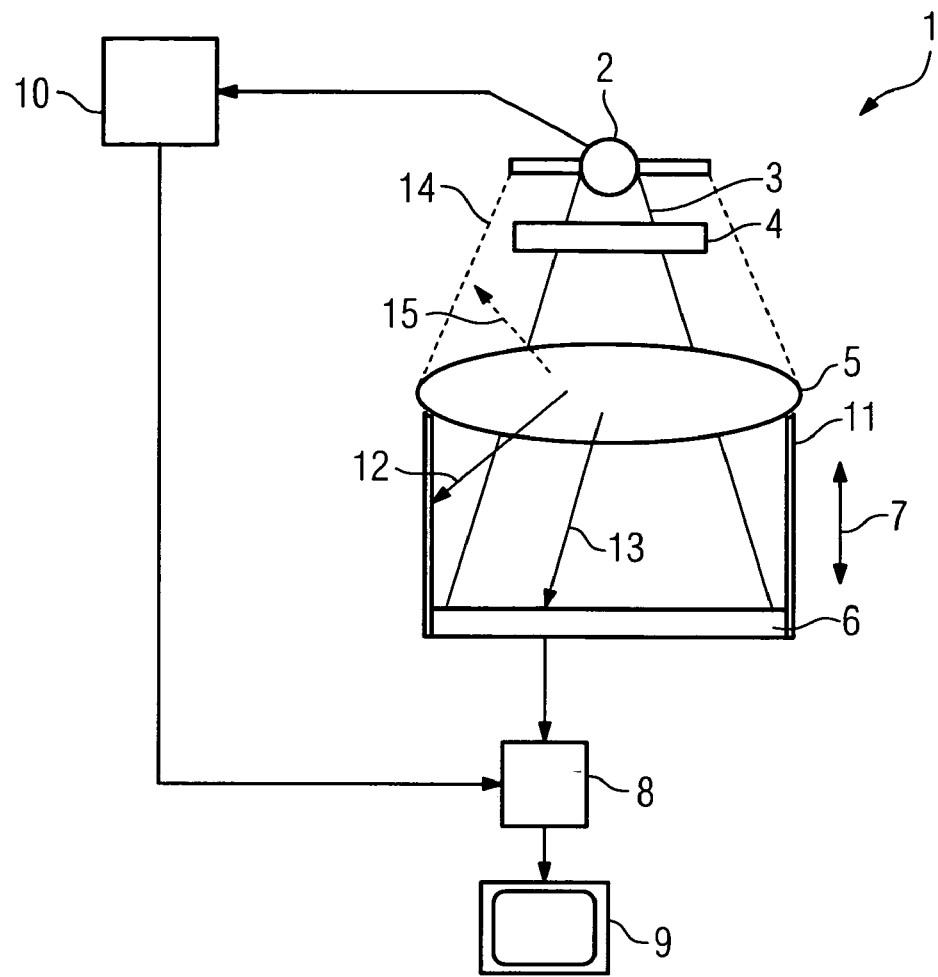
FIG. 1 a schematic sketch of an inventive radiation image capture apparatus of a first embodiment, FIG. 2 a perspective view of a radiation absorption apparatus, FIG. 3 a perspective representation of a wall of the radiation absorption apparatus from FIG. 2, in a first embodiment, FIGS. 4 and 5 a wall version of a radiation absorption apparatus of a second embodiment, FIGS. 6 and 7 a wall embodiment of a scattered radiation absorption apparatus of a third embodiment, and FIG. 8 a schematic representative of a radiation image capture apparatus of a second embodiment.

FIG. 1 shows an inventive radiation image capture apparatus 1, comprising a radiation source 2, for example an x-ray source, which emits x-ray radiation 3 in the shape of a cone, which is filtered via a filter 4. The x-ray radiation strikes an examination object 5, passes through this and is received by a radiation image receptor 6 and converted into corresponding image signals which are read out and processed via an image processing apparatus 8 and output on a monitor 9. The operation of the x-ray source 2 and of the image processing apparatus 8 is controlled via a central control apparatus 10.

At the radiation image receptor 6, which is designed here for example as a solid-state radiation detector, a radiation absorption apparatus 11 is provided which is arranged at the radiation image receptor 6 so as to be moveable via suitable linear guides. The embodiment shown is a rigid radiation absorption apparatus which can be moved in its entirety in the linear guides in respect of the radiation receptor 6, as represented by the double arrow 7. Using the radiation absorption apparatus 11, which is closed on all sides, the distance between the radiation image receptor 6 and the examination object 5 can be spanned and laterally closed. The result of this is that scattered radiation 12, which otherwise would not strike the radiation image receptor 6, strikes the radiation absorption apparatus 11 and is absorbed thereby, and consequently cannot enter the environment, while the primary radiation 13 can strike the radiation image receptor 6 unimpeded.

It should be noted here that in FIG. 1 only the two sides of the radiation absorption apparatus 11 are represented; naturally in the case of a rectangular embodiment the absorption apparatus has four side walls which form a laterally closed cube.

The front edges of the top and bottom side walls can be slightly curved corresponding to the shape of the patient, in order to be brought as close as possible to the patient.

Additionally in FIG. 1 the possibility is al so represented (by a dashed line) of also providing a radiation absorption apparatus 14 at the radiation source 2, said radiation absorption apparatus 14 expanding out in the shape of a cone or truncated pyramid toward the examination object 5 in the example shown. It equally serves to absorb scattered radiation 15, which of course can also be scattered toward the radiation source 2. This radiation absorption apparatus 14 too is closed on all sides. If both radiation absorption apparatuses 11, 14 are provided, the complete beam path from the radiation source 2 to the radiation image receptor 6 is enclosed, so that maximum absorption of scattered radiation is achieved.

Figure 2:
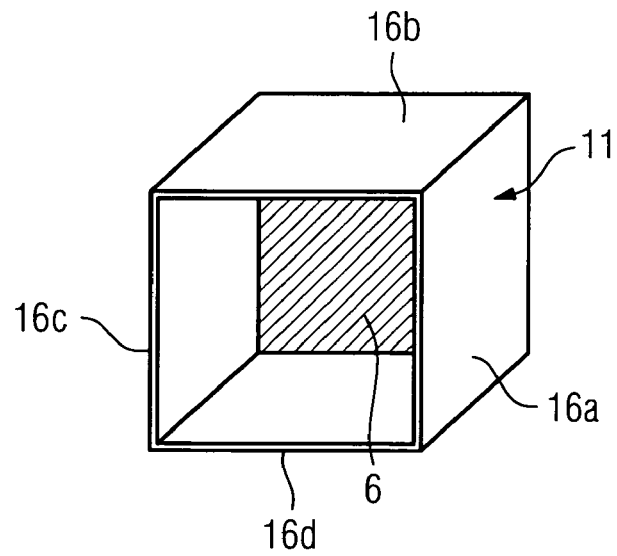

FIG. 2 shows a schematic representation of the radiation absorption apparatus 11 from FIG. 1. It can be seen to have a total of four side walls 16a, 16b, 16c and 16d which form a box which is closed on all sides. Also shown is the radiation image receptor 6, which in this case is rectangular or square, for example the solid-state radiation detector, on which the rigid radiation absorption apparatus 11 can be relocated linearly.

Figure 3:
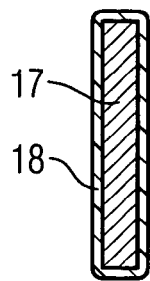

FIG. 3 shows a section through a wall of a radiation absorption apparatus, as shown in FIG. 2, the wall itself being rigid. An absorption element 17 is shown, for example a band-shaped lead element which is accommodated in a sheath 18, for example a plastic jacket.

Figure 4:
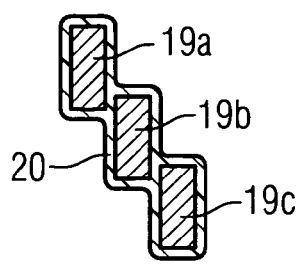
Figure 5:
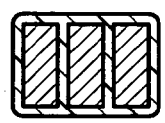

FIGS. 4 and 5 show an alternative wall structure. Here three separate sections 19a, 19b and 19c made of radiation-absorbent material, for example lead, are provided, which are accommodated in a common sheath 20. The sections 19a, b, c are connected to one another (in a manner not shown in greater detail) so as to move together. They can be relocated between the extended position in FIG. 4, in which they are arranged virtually behind one another and offset to one another, and the retracted position in FIG. 5, in which they lie essentially parallel next to one another. The movement linkage can be such that, for example, initially on extension from the closed position in FIG. 5 the section 19a is drawn out of the unit. If it has reached a particular position and if it is moved further, it automatically takes the next section 19b with it, until this has been moved into the end position, in which then the sections are furthest extended.

Figure 6:
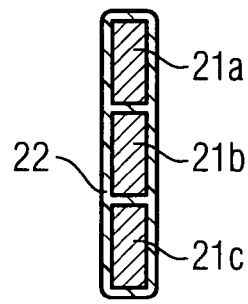
Figure 7:

FIGS. 6 and 7 show another wall embodiment. Here too three absorption sections 21a, 21b and 21c are provided, which are accommodated in a sheath 22, and which here are linked to one another in the manner of an accordion, so that, as FIG. 7 shows, they collapse or fold up virtually in the manner of an accordion. None of the sections is represented to scale. In reality they have e.g. a thickness of 1 mm and a height or length of e.g. 10 cm.

A radiation absorption apparatus can in principle be relocated or generally moved manually. Alternatively, however, it is also conceivable for the movement to be motor-driven, i.e. automatic, such an embodiment being shown in FIG. 8. In the inventive radiation image capture apparatus 23 described there, in which only a radiation absorption apparatus 25 provided at the radiation receptor 24 is provided, a motor 26, which for example can likewise be controlled via the central control apparatus 10, is provided, by means of which the radiation absorption apparatus 25, which for example is rigid in accordance with the embodiment according to FIG. 2, can be relocated automatically in respect of the radiation receptor 24. The means the positioning relative to the examination object 27 takes place automatically. To avoid the radiation absorption apparatus 25 striking the examination object 27 and to detect the optimum positioning in respect of the examination object 27, in the example shown a sensor 28 is provided, which communicates with the control apparatus 10, the control apparatus 10 controlling the motor 26 as a function of the sensor detection. It is expedient in the case of a rectangular box embodiment of the radiation absorption apparatus for example to position such a sensor 28 on each side wall.

Figure 8:
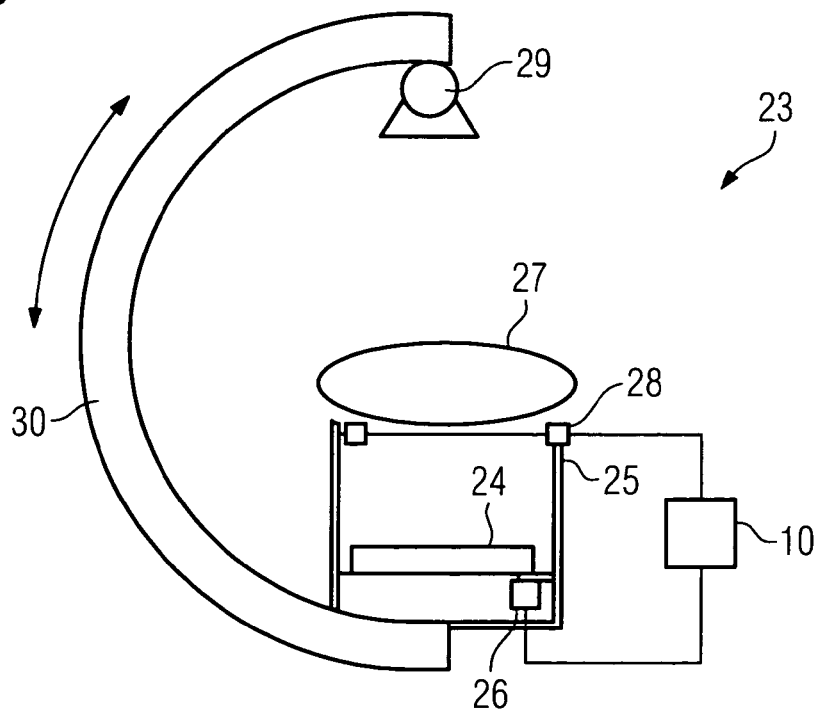

In the embodiment according to FIG. 8 the radiation source 29 and the radiation receptor 24 are arranged on a C-arm 30. This is movable in known manner, as is indicated by the double arrow. To avoid the radiation absorption apparatus 25, which is optimally positioned for a preceding image capture, striking the examination object 27 when such a rotational movement is initiated, the control apparatus 10 is advantageously designed so that the motor 26 can be controlled for a short, quick backward movement of the radiation absorption apparatus 25 from the former capture position, so that there is sufficient clearance between front edge of the radiation absorption apparatus 25 and the examination object 27. The C-arm 30 can now be moved without danger. In the new position the control apparatus 10, controlled via the one or more sensors 28, can then extend and optimally position the radiation absorption apparatus 25 again via the motor 26.

The invention claimed is:

1. A radiation image capture apparatus, comprising:
   a radiation source;
   a radiation detector, wherein an examination object is positioned between the radiation source and the radiation detector when capturing an image;
   a laterally closed radiation absorption apparatus shaped as an apron, the radiation absorption apparatus configured to be moved in a direction towards the examination object and to absorb scattered radiation emitted from the examination object, wherein the radiation absorption apparatus is arranged at the radiation source or at the radiation detector;
   at least one drive motor for moving the radiation absorption apparatus; and
   a control apparatus for controlling the drive motor,
   further comprising at least one sensor for detecting a current position of the radiation absorption apparatus relative to the examination object, the sensor connected to the control apparatus such that the control apparatus controls the movement of the radiation absorption apparatus based on the detected position.

2. The radiation image capture apparatus according to claim 1, wherein the radiation absorption apparatus is further configured to be moved linearly relative to the radiation source or relative to the radiation detector.

3. The radiation image capture apparatus according to claim 2, wherein the radiation absorption apparatus is rigid and supported at the radiation source or at the radiation detector for moving the radiation absorption apparatus laterally relative to the examination object.

4. The radiation image capture apparatus according to claim 1, wherein the radiation absorption apparatus comprises a plurality of sections connected to each other and movable relative to each other, the sections having a retracted and an extended position, wherein the sections are arranged parallel to each other when arranged in the retracted position and one behind the other when arranged in the extended position.

5. The radiation image capture apparatus according to claim 1, wherein the radiation absorption apparatus is configured to be collapsed or folded up.

6. The radiation image capture apparatus according to claim 5, wherein the radiation absorption apparatus is configured to be collapsed according to the principle used with an accordion.

7. The radiation image capture apparatus according to claim 1, wherein the radiation absorption apparatus includes a plurality of swivel-mounted sections configured to be swiveled into a recording position such that the plurality of swivel-mounted sections form a laterally closed shape when swiveled into the recording position.

8. The radiation image capture apparatus according to claim 1, further comprising a moveable C-shaped arm, wherein
the radiation source and the radiation detector are arranged on the C-shaped arm, and
the radiation absorption apparatus is configured to:
be moved away from the examination object by the control apparatus for avoiding a collision with the examination object upon detecting an imminent movement of the C-shaped arm; and
to be moved towards the examination object by the control apparatus when the C-shaped arm has reached a new recording position.

9. The radiation image capture apparatus according to claim 1, wherein the radiation absorption apparatus comprises band- or plate-shaped lead accommodated in a sheath for absorbing radiation.

10. The radiation image capture apparatus according to claim 1, wherein the radiation absorption apparatus comprises lead accommodated in a transparent material so that the radiation absorption apparatus is transparent.

11. The radiation image capture apparatus according to claim 10, wherein the radiation absorption apparatus comprises lead glass.

* * * * *